United States Patent
Wortman et al.

(10) Patent No.: US 11,439,530 B2
(45) Date of Patent: Sep. 13, 2022

(54) SHOWER SLING

(71) Applicant: SHOWER90 LLC, Mansfield, OH (US)

(72) Inventors: Ivan J. Wortman, St. Marys, PA (US); Mitchell W. Cox, Newark, OH (US)

(73) Assignee: SHOWER90 LLC, Mansfield, OH (US)

( * ) Notice: Subject to any disclaimer, the term of this patent is extended or adjusted under 35 U.S.C. 154(b) by 371 days.

(21) Appl. No.: 16/170,507

(22) Filed: Oct. 25, 2018

(65) Prior Publication Data

US 2019/0117439 A1    Apr. 25, 2019

Related U.S. Application Data

(60) Provisional application No. 62/576,694, filed on Oct. 25, 2017.

(51) Int. Cl.
*A61F 5/37* (2006.01)

(52) U.S. Cl.
CPC .................. *A61F 5/3738* (2013.01)

(58) Field of Classification Search
CPC .... A61F 5/3738; A61F 5/3746; A61F 5/3753; A61F 5/37; A61F 5/3723; A61F 5/0118; A61F 5/013; A61F 5/05866; A61F 5/05858; A61F 5/3715; A61F 5/373; A63B 69/0028; A63B 69/0059
USPC ............... 602/4, 21, 20; 2/44–45; 224/901.4
See application file for complete search history.

(56) References Cited

U.S. PATENT DOCUMENTS

| | | | |
|---|---|---|---|
| 2,560,243 A | 7/1951 | Peterson | |
| 2,616,419 A | 11/1952 | Karfiol | |
| 2,935,066 A | 5/1960 | Holloway | |
| 3,307,538 A * | 3/1967 | Groll | A61F 5/3738 602/4 |
| 3,491,726 A | 1/1970 | Partin | |
| 3,730,164 A * | 5/1973 | Rash | A61F 5/3738 602/4 |

(Continued)

OTHER PUBLICATIONS https://amzn.to/2lgtXe3—Triangle Dislocated Arm Sling Medical Shoulder Immobilizer Rotator Cuff Wrist Elbow Forearm Support Brace Strap with Soft Comfortable Padded Lightweight Simple for Broken & Fractured Arm; By TANDCF.

(Continued)

*Primary Examiner* — Rachael E Bredefeld
*Assistant Examiner* — Trisha Talapatra
(74) *Attorney, Agent, or Firm* — Jacob M. Ward; Ward Law Office LLC (57) ABSTRACT

An arm sling has a neck strap that is selectively slidably secured to a first arm strap and a second arm strap. The arm sling is adapted for use in the shower and is configured to be adjusted using a single arm. Each of the arm straps has a loop and a belt. An outer surface of each loop may be covered with a first fastening portion and the belt may be covered with a second fastening portion. The first fastening portion is configured to removably connect with the second fastening portion at a plurality of locations along a length of the second fastening portion. The loop also has a securement band disposed adjacent a junction between the belt and the loop. The securement band is configured to selectively hold the belt adjacent to the loop.

14 Claims, 4 Drawing Sheets

(56) References Cited

U.S. PATENT DOCUMENTS

| | | | |
|---|---|---|---|
| 4,337,938 A * | 7/1982 | Rodriguez | A63B 69/0059 224/258 |
| 4,355,635 A | 10/1982 | Bihl et al. | |
| 4,625,719 A * | 12/1986 | Chambers | A61F 5/3738 128/DIG. 15 |
| 5,592,692 A | 1/1997 | Larson | |
| 5,848,956 A * | 12/1998 | Grettner | A63B 21/4017 482/69 |
| 6,110,133 A * | 8/2000 | Ritts | A61F 5/3738 128/DIG. 19 |
| 6,190,340 B1 * | 2/2001 | Borell | A61F 5/3738 2/44 |
| 6,230,711 B1 * | 5/2001 | Maisnik | A61F 13/0273 128/869 |
| 6,311,346 B1 * | 11/2001 | Goldman | A61F 5/37 128/876 |
| 6,929,164 B1 * | 8/2005 | Thomas | A45C 13/30 224/148.4 |
| 7,789,842 B2 | 9/2010 | Bittar | |
| 2008/0228116 A1 * | 9/2008 | Walker | A61F 5/3738 602/4 |
| 2016/0074205 A1 * | 3/2016 | Yao | A61F 5/3738 602/4 |
| 2018/0228637 A1 * | 8/2018 | Elzik | A61F 5/3738 |
| 2019/0015248 A1 * | 1/2019 | Russell | A61F 7/02 |

OTHER PUBLICATIONS https://amzn.to/2Km8Rrm—Zinnor Triangle Dislocated Arm Sling Medical Shoulder Immobilizer Rotator Cuff Wrist Elbow Forearm Support Brace Strap with Soft Comfortable Padded Lightweight Simple for Broken & Fractured Arm; By ZINNOR.

https://amzn.to/2GiteDC—Triangle Dislocated Arm Sling Medical Shoulder Immobilizer Rotator Cuff Wrist Elbow Forearm Support Brace Strap with Soft Comfortable Padded Lightweight Simple for Broken & Fractured Arm; By TODDOBRA.

Yosoo "Yosoo Arm Sling" Amazon.com, published on Nov. 28, 2016 (Nov. 28, 2016), retrieved on Dec. 27, 2018 (Dec. 27, 2018), accessed at https://www.amazon.com/Yosoo-Arm-Sling-Immobilizer-Lightweight/dp/B01M19DIYS, entire document, especially p. 1 Figure; p. 9-13 Figures; p. 1, para 1, p. 5, para 5.

Ashland University College of Business "Executive Eagle Fall 2017" ISSUU, published on Oct. 4, 2017 (Oct. 4, 2017), retrieved on Dec. 27, 2018 (Dec. 27, 2018), accessed at https://issuu.eom/ashlanduniversitycollegeofbusiness/docs/exec_eagle_fall_2017_10.4.17/23, entire document, especially Slides 22-23.

* cited by examiner

SHOWER SLING

CROSS REFERENCE TO RELATED APPLICATIONS

This application claims the benefit of U.S. Provisional Application Ser. No. 62/576,694, filed on Oct. 25, 2017. The entire disclosure of the above application is hereby incorporated herein by reference.

FIELD

The present disclosure relates to a sling and, more specifically, a water-resistant sling for use in the shower.

BACKGROUND

Slings are often used to provide support to an injured arm, hand, wrist, elbow, or shoulder, sometimes in conjunction with a cast. The use of arm slings following surgery of the arm, hand, wrist, elbow or shoulder is typically recommended to optimize recovery times and ensure the effectiveness of the surgical procedure.

The use of cloth for slings is well known. Various strap and buckle arrangements are also known for use with cloth slings. These arrangements permit adjustments of the slings to accommodate different arm orientations and heights. However, adjusting the length of the slings may be difficult, particularly when only able to use a single hand. To complicate matters further, showering in slings may be troublesome. The moisture may provide an environment for disease-causing microbes to grow, which may infect the injured limb.

To mitigate against the growth of disease-causing microbes, a surface area of the sling is often minimized. Slings that use strap systems with minimal surface area are known in the art. For example, U.S. Pat. No. 2,935,066 to Marion teaches a supporting loop adapted to fit over the neck of the wearer, where one sling loop may support the wrist of the wearer, while the other sling loop supports the forearm of the wearer. In a further example, U.S. Pat. No. 2,616,419 to Karfiol teaches a sling that may be made from a single long strip of tape stock, where one end is provided with a fixed loop, and the other end is provided with an adjustable loop.

Furthermore, after a patient undergoes shoulder or elbow surgery, for example, a physician typically instructs the patient to not shower until at least the third day after the procedure. When the patient is permitted to shower, the patient is taught to keep the arm at a 90-degree angle. However, keeping the arm at a healthy and comfortable 90-degree angle while taking a shower may be difficult without a sling.

There is a continuing need for an arm sling that may be adjusted using a single arm, and which is adapted for use in the shower. Desirably, the arm sling has minimal surface area to militate against fungal or bacterial growth.

SUMMARY

In concordance with the instant disclosure, an arm sling that may be adjusted using a single arm, which is adapted for use in the shower, and which has minimal surface area to militate against fungal or bacterial growth, has been surprisingly discovered.

In one embodiment, an arm sling has a neck strap with a first end and a second end. A first arm strap is connected to the first end of the neck strap. The arm sling also has a second arm strap that is selectively slidably connected to the second end of the neck strap. The second arm strap has a belt and a loop. The belt has a first fastening portion, and the loop has a second fastening portion. The first fastening portion is configured to removably connect with the second fastening portion at a plurality of locations along a length of the second fastening portion. This allows for a distance between the loop and the second end of the neck strap to be selectively varied. The second arm strap further includes a securement band that is disposed adjacent to a junction between the belt and the loop. The securement band is affixed to the loop and is configured to selectively hold the belt adjacent to the loop.

In another embodiment, an arm sling has a neck strap with a first end and a second end. The arm sling has a first arm strap selectively slidably connected to the first end of the neck strap, and a second arm strap selectively slidably connected to the second end of the neck strap. The first arm strap and the second arm strap each have a belt and a loop. The belt has a first surface, and a second surface. The belt also has a first fastening portion secured to the first surface. The loop has an inner surface and an outer surface. The loop also has a second fastening portion secured to the outer surface. The first fastening portion is configured to removably connect to the second fastening portion at a plurality of locations along a length of the second fastening portion, which selectively varies a distance between the loop and the neck strap. The second arm strap further includes a securement band affixed to the inner surface of the loop adjacent a junction between the belt and the loop. The securement band has a first free end and a second free end. The first free end is configured to removably connect to the second free end. The securement band is adapted to selectively hold the belt adjacent to the loop.

In a further embodiment, a method of adjusting the arm sling includes a first step of providing the arm sling. The arm sling has a neck strap with a first end and a second end. A first arm strap is connected to the first end of the neck strap. The arm sling also has a second arm strap that is selectively slidably connected to the second end of the neck strap. The second arm strap has a belt and a loop. The belt has a first fastening portion, while the loop has a second fastening portion. The first fastening portion is configured to removably connect with the second fastening portion at a plurality of locations along a length of the second fastening portion, which selectively varies a distance between the loop and the second end of the neck strap. The second arm strap further includes a securement band that is disposed adjacent to a junction between the belt and the loop. The securement band is affixed to the loop and is configured to selectively hold the belt adjacent to the loop. The method further includes a second step of placing the neck strap around a neck. In a third step, an arm of the user is inserted into the first arm strap, until the first arm strap abuts a forearm of the user. A fourth step of the method includes inserting the arm of the user into the loop of the second arm strap, until the loops abuts a wrist of the user. A fifth step of the method includes moving a terminal end of the belt from one of the plurality of locations on the loop to another of the plurality of locations on the loop. The movement of the terminal end varies the distance between the loop and the second end of the neck strap. In a sixth step, the first fastening portion of the belt is connected to the second fastening portion of the loop, whereby the arm sling is adjusted for the user.

In an exemplary embodiment, a method of using the arm sling can include a first step of locating a tag on the arm sling that details which side of the arm sling is to face the body in use. Then, the user carefully positions the adjustable loop around the forearm region. This placement ensures the arm sling will not slip off the forearm or elbow. In a second step, the user brings the padded portion of the sling around the back of the neck. In a third step, the user fastens the second loop around either the palm or the wrist area. The loop can be held in in the hand or may just rest on the wrist of the user. In a fourth step, the user adjusts the arm sling as necessary to keep the arm at a 90-degree angle using the hook-and-loop fasteners on the belt and loop. To shorten, the user detaches the belt from the loop and pulls or lowers the belt before reattaching. To length, the user detaches the belt form the loop and raises the belt before reattaching. In a fifth step, after the arm sling is adjusted to hold the user's arm at the 90-degree angle, the user firmly attaches the securement band fasteners around the straps to provide additional strap securement. It should be appreciated that after completing the first through fifth steps, the arm sling may not need to be adjusted again for the individual user. In a sixth step, the user may rest their injured arm on a stable surface. Then, the user may carefully remove the strap from their palm, using their uninjured arm. Using the uninjured arm, the user may lift the strap off their next and set it down. Then, the user may carefully slide the second loop off the user's forearm and hand. Finally, in a sixth step, after using the arm sling, the user may hang the arm sling to dry in an area out of reach from children, for example. A bucket may be placed on the floor underneath the arm sling to militate against a wet floor surface. Hanging the arm sling from a showerhead may also be performed.

DRAWINGS

The above, as well as other advantages of the present disclosure, will become readily apparent to those skilled in the art from the following detailed description, particularly when considered in the light of the drawings described herein.

DETAILED DESCRIPTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical unless otherwise disclosed.

FIGS. 1-8 illustrate an arm sling 2 that is adjustable using a single arm, while another arm is supported within the sling 2. The arm sling 2 may have a neck strap 4 with a first end 6 and a second end 8. The first end 6 of the neck strap 4 and the second end 8 of the neck strap 4 are each configured to selectively slidably connect with a first arm strap 10 or a second arm strap 12. For example, the neck strap 4 may be connected by buckles 14 to each of the arm straps 10, 12. However, other suitable types of connectors such as loops, rings, or snaps may also be chosen by a skilled artisan, as desired.

With continued reference to FIGS. 1-8, each arm strap 10, 12 may have a loop 16 and a belt 18. In certain embodiments, as shown in FIGS. 1-2 and 5-8, the arm straps 10,12 may be created by joining the loop 16 to the belt 18 at a junction 20. The junction 20 may be created by stitching, adhesive, sonic welding, or any other suitable method chosen by a skilled artisan.

Each loop 16 may be configured to support a wrist 22 or a forearm 24 of a user, for example, as shown in FIGS. 5-8. The loop 16 may have an inner surface 11, and an outer surface 13 that is disposed opposite the inner surface 11. The belt 18 may have a first surface 15, and a second surface 17 that is disposed opposite the first surface 15. Additionally, in certain embodiments, the first arm strap 10 may be identical in structure and operation to the second arm strap 12. However, it should be appreciated that the first arm strap 10 and the second arm strap 12 need not be identical within the scope of the present disclosure.

Figure 2:
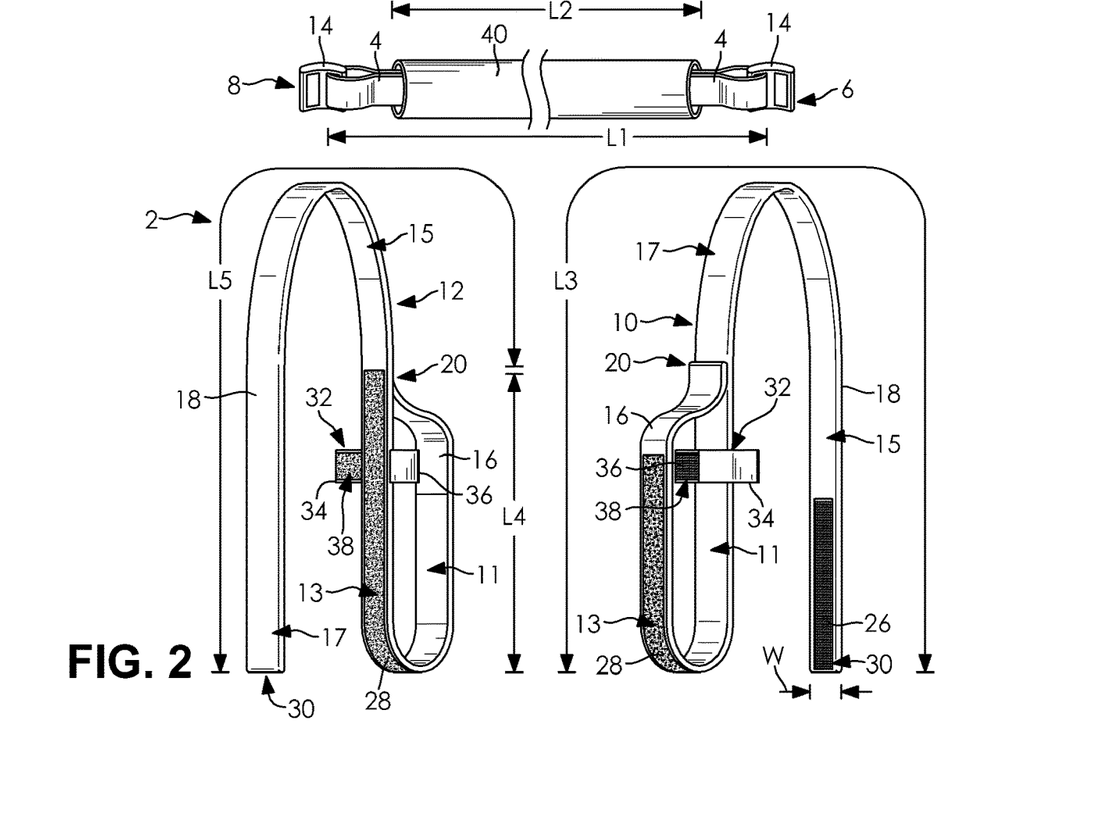
FIG. 2 is a fragmentary perspective view of the arm sling shown in FIG. 1, the arm sling shown disassembled with a neck strap disconnected and illustrated separate from a first arm strap and a second arm strap, the neck strap being shown from a front perspective, the first arm strap being shown from a rear perspective, and the second arm strap being shown from a front perspective for purposes of illustration.
Figure 3:
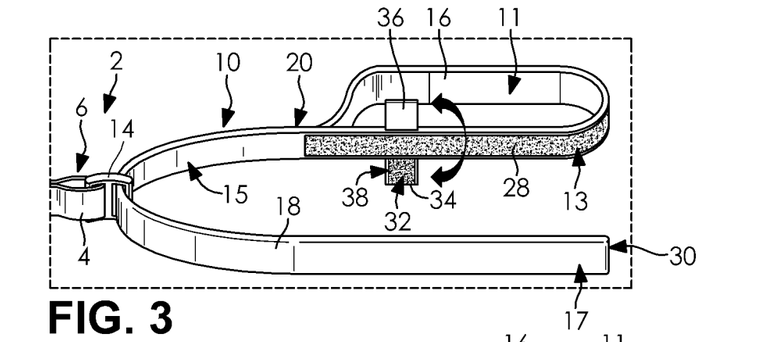
FIG. 3 is an enlarged fragmentary front perspective view of the arm sling taken at callout A in FIG. 1, the arm sling shown with a first fastening portion of a belt disconnected from a second fastening portion of a loop.
Figure 4:
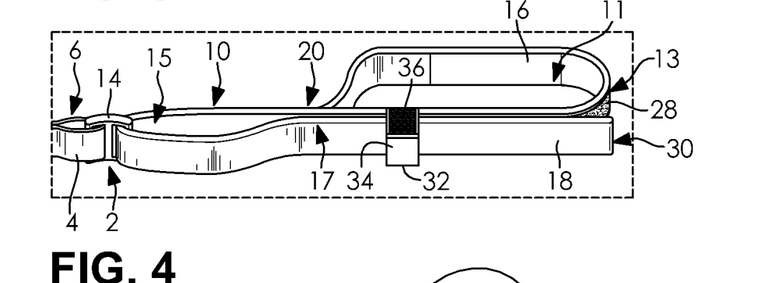
FIG. 4 is an enlarged fragmentary front perspective view of the arm sling shown in FIG. 3, and further illustrated with the first fastening portion of the belt connected to the second fastening portion of the loop.

With reference to FIGS. 3 and 4, the first surface 15 of the belt 18 is configured to selectively adhere to the outer surface 13 of the loop 16. For example, as shown in FIG. 2, the first surface 15 of the belt 18 may have a first fastening portion 26, and the outer surface 13 of the loop 16 may be have a second fastening portion 28. The first fastening portion 26 is configured to selectively attached with the second fastening portion 28. As a non-limiting example, the first and second fastening portions 26, 28 may be hook-andloop fasteners. One skilled in the art may also select other suitable types of fasteners such as magnets, buttons or snaps, as desired.

The first fastening portion 26 and the second fastening portion 28 may be disposed continuously or intermittently along the belt 18 and the loop 16, respectively. In certain embodiments, the second fastening portion 28 may cover a major portion of the loop 16. For example, the second fastening portion 28 may be secured to the outer surface 13 of the loop 16 and disposed between the junction 20 where the loop 16 connects with the first surface 15 of the belt 18 and a portion of the loop 16 adjacent to but spaced apart from the junction 20 where the loop 16 connects with the second surface 17 of the belt 18. In other words, an end of the second fastening portion 28 may be spaced apart from the junction 20.

It should be appreciated that the first fastening portion 26 of the belt 18, shown in FIG. 2, may be removably fastened to the loop 16 in a plurality of positions along a length of the second fastening portion 28 on the outer surface 13 of the loop 16. The fastening of the belt 18 to the loop 16 in multiple positions allows a user to adjust a position of the loop 16 relative to the neck strap 4. For example, the position of the loop 16 may be adjusted relative to the neck strap 4 by altering a location or placement of a terminal end 30 of the belt 18 on the loop 16.

With reference to FIG. 4, the belt 18 may be disposed through a securement band 32. The securement band 32 facilitates a positioning and retainment of the belt 18 in a position where the belt 18 is removably connected to the loop 16. Additionally, the securement band 32 may further militate against an inadvertent disconnection of the belt 18 from the loop 16, where the first fastening portion 26 is removably affixed the second fastening portion 28.

In certain embodiments, the securement band 32 may have a first free end 34 and a second free end 36. The first free end 34 is configured to be removably connected to the second free end 36, for example, using a fastener 38 disposed at each of the first and second free ends 34, 36. The fastener 38 may be a hook-and-loop fastener, magnets, buttons, snaps, or any other fastener 38 chosen by a skilled artisan. It should be appreciated that the fastener 38 disposed on the first free end 34 may be disposed on a side of the securement band 32 opposite a side of the securement band 32 on which the fastener 38 is disposed on the second free end 36.

Figure 1:
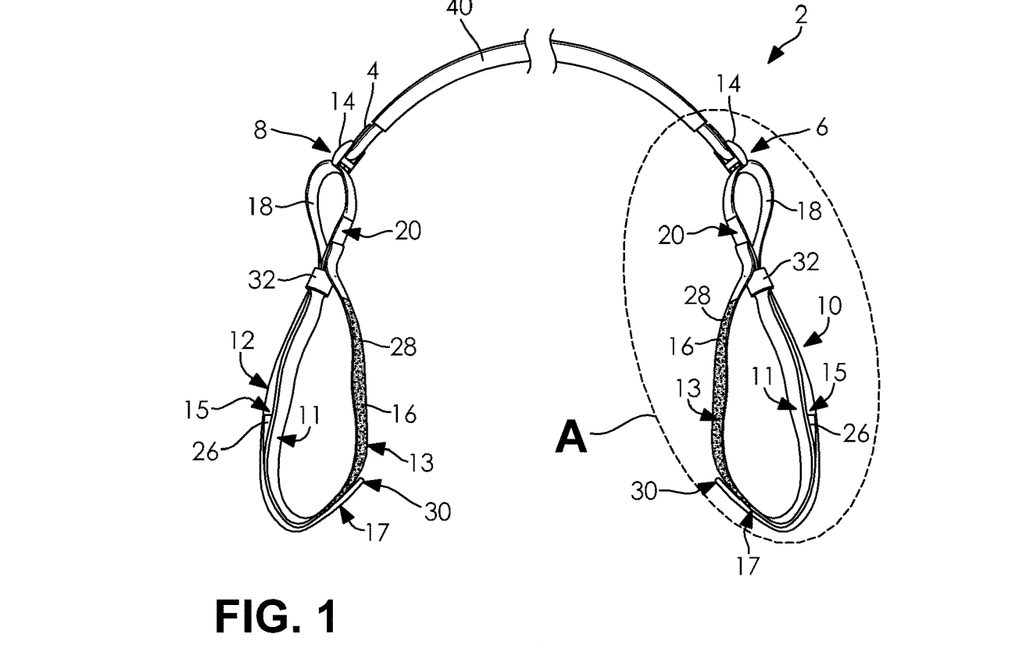
FIG. 1 is a fragmentary front perspective view of an arm sling according to one embodiment of the present disclosure.

An inner portion of the securement band 32, which is disposed between the first and second free ends 34, 36, may also be attached to the inner surface 11 of the loop 16. For example, the inner portion of the securement band may be affixed to the loop 16 adjacent to the junction 20, as shown in FIG. 1. As further non-limiting examples, the securement band 32 may be attached to the loop 16, by stitching, adhesives, sonic welding, or through a variety of other suitable methods, as desired.

In particular embodiments, as shown in FIGS. 1-8, the neck strap 4 may be covered in a gripping sleeve 40 to militate against slippage in a wet environment. The gripping sleeve 40 may also provide padding for comfort in wearing the arm sling 2. For example, the neck strap 4 may have a gripping sleeve 40 manufactured from neoprene or polychloroprene, as a non-limiting example. A skilled artisan may also select other suitable materials and configurations for the gripping sleeve 40 within the scope of the present disclosure. In a further example, the neck strap 4 may have inherent gripping properties, or may be coated with a suitable material that facilitates gripping of the neck strap 4 and minimizes slippage, and may not require the gripping sleeve 40 to militate against slippage in the wet environment.

With reference to FIG. 2, in one example, a length L1 of the neck strap 4 may be between about fourteen (14) inches and about twenty (20) inches, and in a most particular example, the length L1 of the neck strap 4 may be about seventeen (17) inches. For example, the gripping sleeve 40 may be of a length L2 between about twelve (12) inches and about sixteen (16) inches, and most particularly, the gripping sleeve 40 may be about fourteen (14) inches in length L2. In another example, the total length of the arm straps 10, 12, including the belt 18 and the loop 16 where connected, may be of a length L3 between about twenty-one (21) inches and about thirty-three (33) inches, or more specifically, the arm straps 10, 12 may be about twenty-seven (27) inches in length L3. In a further example, the loop 16 of each arm strap 10, 12 may be of a length L4 between about seven (7) inches and about eleven (11) inches, and more specifically, the length L4 of the loop 16 may be about nine (9) inches. In another example, the belt 18 of each arm strap 10, 12 may be of a length L5 between about fourteen (14) inches and about twenty-two (22) inches, and more specifically, the length L5 of the belt 18 may be approximately eighteen (18) inches. One of ordinary skill in the art may also select other suitable dimensions for the various components of the arm sling, as desired.

In operation, and according to the method of the disclosure illustrated in FIGS. 5-8, the arm sling 2 may be used to support the arm of the user, and may also be adjusted by the user to comfortably support and orient the arm at roughly a 90-degree angle.

Figure 5:
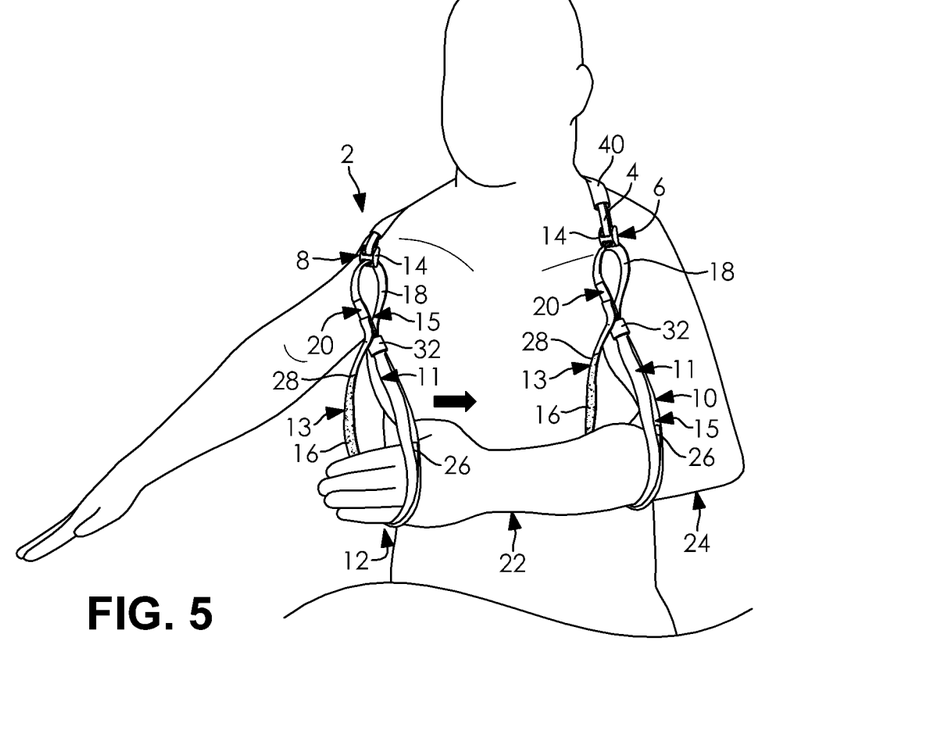
FIG. 5 is a front perspective view of the arm sling shown in FIG. 1, the arm sling further illustrated in an initial step of being worn by a user, with a forearm of the user resting in the loop of the first arm strap, while the user inserts a hand into the loop of the second arm strap.
Figure 6:
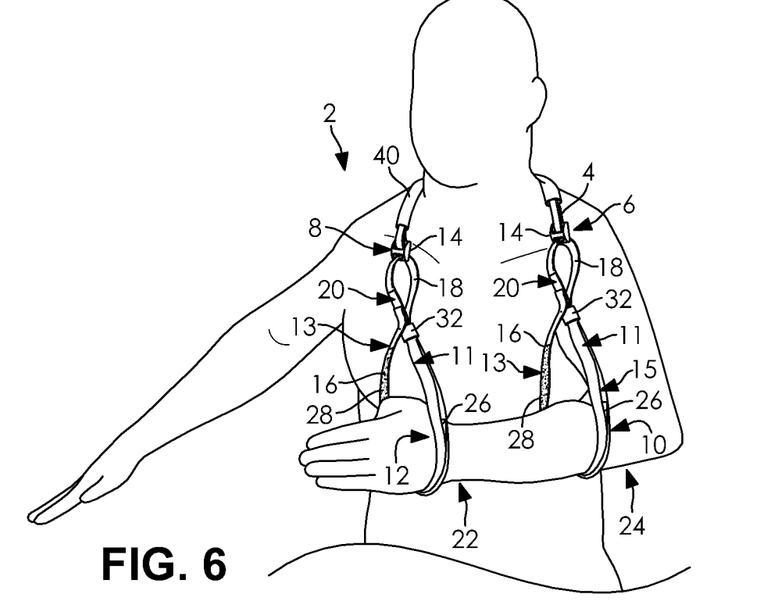
FIG. 6 is a front perspective view of the arm sling shown in FIG. 1, the arm sling further illustrated in another step of being worn by the user, with the forearm of the user resting in the loop of the first arm strap, and the loop of the second arm strap supporting a wrist.

As shown in FIG. 5, the neck strap 4 is placed around the user's neck in a first step. The loop 16 of the first arm strap 10 is then moved to cradle the forearm 24 of a first arm of the user. In a second step, the user then inserts a hand of the first arm into the loop 16 of the second arm strap 12, until the loop 16 abuts the wrist 22, as shown in FIG. 6.

Figure 7:
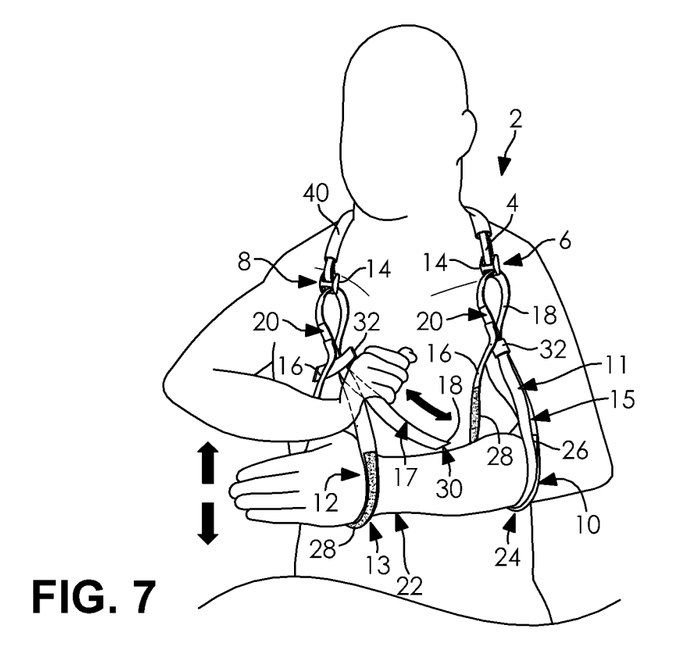
FIG. 7 is a front perspective view of the arm sling shown in FIG. 1, the arm sling further illustrated in a further step of being worn by the user, with the forearm of the user resting in the loop of the first arm strap, the loop of the second arm strap supporting the wrist, and the user disconnecting the first fastening portion of the belt from the second fastening portion of the loop on the second arm strap for adjustment purposes.

The user may then adjust the second arm strap 12 with a second arm in a third step by gripping the belt 18, and detaching the first fastening portion 26 from the second fastening portion 28, as shown in FIG. 7. The user may then move the terminal end 30 of the belt 18, altering the position of the loop 16 of the second arm strap 12 relative to the second end 8 of the neck strap 4. In this manner, the loop 16 of the second arm strap 12 may be used to raise or lower the wrist 22 of the first arm of the user until the first arm is at a comfortable or desired angle, such as 90-degrees.

Figure 8:
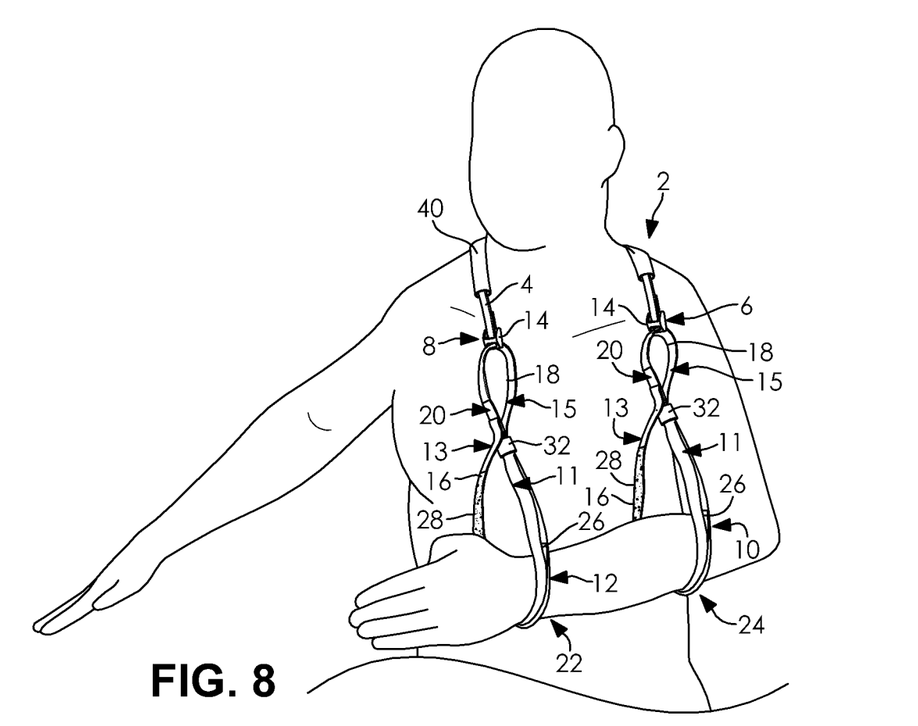
FIG. 8 is front perspective view of the arm sling shown in FIG. 1, the arm sling further illustrated in a yet another step of being worn by the user, with the forearm of the user resting in the loop of the first arm strap, the loop of the second arm strap supporting the wrist, the first fastening portion of the belt re-connected by the user to the second fastening portion of the loop of the second arm strap, so that the arm of the user is at a different position than the position of the arm shown in FIG. 7.

In a fourth step, the user may then reattach the second fastening portion 28 of the belt 18 to the first fastening portion 26 of the loop 16 so the terminal end 30 is at the desired position, as shown in FIG. 8. The first arm of the user is thereby secured and provided at an angle suitable for healing.

The ability to adjust an elevation of the loop 16 relative to the neck strap 4 enables the arm sling 2 to accommodate different arm orientations and heights. For example, the arm straps 10, 12 may be adjusted to keep the arm at a 90-degree angle to facilitate the healing of an injury, for example, following surgery.

After the first fastening portion 26 is removably connected to the second fastening portion 28, a user may further fasten the first free end 34 of the securement band 32 to the second free end 36 of the securement band 32 in a fifth step, as shown in FIGS. 3-4. The fifth step advantageously militates against the inadvertent disconnection of the first fastening portion 26 from the second fastening portion 28 in use.

It should be appreciated that the first through fifth steps described herein may also be performed with respect to the first arm strap 10, for further adjustment by the user. This further adjustment permits for use of the arm sling 2 with a wide variety of body types, including heights and sizes of the user. In alternate embodiments, one of the first and second arm straps 10, 12 may be static in nature, and not adjustable, thereby permitting for adjustment through manipulation of only one of the first and second arms straps 10, 12.

Advantageously, the arm sling 2 may be worn when bathing or showering. The neck strap 4 and arm straps 10, 12 may each have a minimal surface area compared to cloth slings known in the art for supporting the entire arm. For example, as shown in FIG. 2, the neck strap 4, the first arm strap 10, and the second arm strap 12 may each be between about one-half (½) inch in width and about two (2) inches in width, and most particularly about one (1) inch wide W. The minimal surface area militates against fungal and bacterial growth on the arm sling 2. The minimal surface area further mitigates a risk of user getting an infection from the arm sling 2.

In a particular embodiment, the neck strap 4 and arm straps 10, 12 are each formed from a water-resistant material such as nylon, polyester, acrylic, vinyl, polyurethane laminate, thermoplastic polyurethane, laminated cotton, or wool materials. The water-resistance may also be provided in the form of a coating of such a material disposed on at least a portion of the arm sling 2. However, a skilled artisan may select other suitable water-resistant materials for the arm straps 10, 12 within the scope of the present disclosure. These materials may also be provided with antimicrobial agents, either compounded in the materials or coated on the materials, as desired. Additionally, one of ordinary skill in the art understands that the arm sling 2 may also be used in dry conditions to facilitate a healing of an injury, for example, immediately following a surgical procedure.

Most advantageously, the arm sling 2 of the present disclosure may be adjusted using a single arm, is adapted for use in the shower, and may have a minimal surface area to mitigate fungal or bacterial growth on the arm sling 2.

While certain representative embodiments and details have been shown for purposes of illustrating the invention, it will be apparent to those skilled in the art that various changes may be made without departing from the scope of the disclosure, which is further described in the following appended claims.

What is claimed is:

1. An arm sling for supporting a wrist and/or a forearm of a user, comprising:
   a single neck strap having a first end and a second end;
   a gripping sleeve through which the single neck strap is disposed, the gripping sleeve being an elongate tube;
   a first arm strap configured to be reversibly coupled to the first end of the single neck strap; and
   a second arm strap configured to be reversibly coupled to the second end of the single neck strap, the second arm strap including:
      a belt configured to be selectively slidably connected to the second end of the single neck strap, the belt including a first fastening portion;
      a loop with an inner surface and an outer surface and joined to the belt at a junction, the loop including a second fastening portion, the first fastening portion configured to removably connect with the second fastening portion at a plurality of locations along a length of the second fastening portion to selectively vary a distance between the loop and the second end of the single neck strap, the loop configured to be positioned around and support the wrist and/or the forearm of the user, wherein the loop is coupled to the belt and the belt is reversibly coupled to the single neck strap; and
      a securement band disposed adjacent the junction joining the belt and the loop, the securement band affixed to the loop and configured to selectively hold the belt adjacent to the loop, wherein the securement band is attached to the inner surface of the loop;
   wherein the first arm strap is configured to support one of the wrist and the forearm of the user and the loop of the second arm strap is configured to support the other of the wrist and/or the forearm of the same arm of the user,
   wherein the single neck strap is between about 14 inches and about 20 inches in length, the first arm strap and the second arm strap are each between about 21 inches and about 33 inches in length, and the single neck strap, the first arm strap, and the second arm strap are each between about ½ inch wide and about 2 inches wide.

2. The arm sling of claim 1, wherein the first arm strap includes:
   a belt configured to be selectively slidably connected to the first end of the single neck strap, the belt including a first fastening portion;
   a loop joined to the belt at a junction, the loop including a second fastening portion, the first fastening portion configured to removably connect with the second fastening portion at a plurality of locations along a length of the second fastening portion to selectively vary a distance between the loop and the second end of the single neck strap, the loop configured to be positioned around and support the wrist and/or the forearm of the user; and
   a securement band disposed adjacent the junction joining the belt and the loop, the securement band affixed to the loop and configured to selectively hold the belt adjacent to the loop.

3. The arm sling of claim 1, wherein the belt has a first surface and a second surface, the first fastening portion is disposed on the first surface of the belt, the loop has an outer surface, and the second fastening portion is disposed on the outer surface of the loop.

4. The arm sling of claim 3, wherein the second fastening portion extends along a major portion of the loop.

5. The arm sling of claim 4, wherein an end of the second fastening portion is spaced apart from the junction.

6. The arm sling of claim 1, wherein the securement band has a first free end and a second free end, the first free end configured to be removably connected to the second free end.

7. The arm sling of claim 1, wherein the first end of the single neck strap is connected to a first buckle and the second end of the single neck strap is connected to a second buckle.

8. The arm sling of claim 7, wherein a belt of the first arm strap is selectively slidably disposed through the first buckle, and the belt of the second arm strap is selectively slidably disposed through the second buckle.

9. The arm sling of claim 1, wherein the single neck strap, the first arm strap, and the second arm strap are each formed from nylon.

10. The arm sling of claim 1, wherein the gripping sleeve is formed from neoprene.

11. The arm sling of claim 1, wherein the first fastening portion and the second fastening portion are configured as hook-and-loop fasteners.

12. An arm sling for supporting a wrist and/or a forearm of a user, comprising:
a single neck strap having a first end and a second end;
a gripping sleeve through which the single neck strap is disposed, the gripping sleeve being an elongate tube;
a first arm strap configured to be reversibly coupled to the first end of the single neck strap; and
a second arm strap configured to be reversibly coupled to the second end of the single neck strap, the second arm strap including:
a belt configured to be selectively slidably connected to the second end of the single neck strap, the belt including a first fastening portion;
a loop with an inner surface and an outer surface and joined to the belt at a junction, the loop including a second fastening portion, the first fastening portion configured to removably connect with the second fastening portion at a plurality of locations along a length of the second fastening portion to selectively vary a distance between the loop and the second end of the single neck strap, the loop configured to be positioned around and support the wrist and/or the forearm of the user, wherein the loop is coupled to the belt and the belt is reversibly coupled to the single neck strap; and
a securement band disposed adjacent the junction joining the belt and the loop, the securement band affixed to the loop and configured to selectively hold the belt adjacent to the loop, wherein the securement band is attached to the inner surface of the loop;
wherein:
the belt has a first surface and a second surface, the first fastening portion is disposed on the first surface of the belt, the loop has an inner surface and an outer surface, and the second fastening portion is disposed on the outer surface of the loop;
the second fastening portion extends along a major portion of the loop; and
an end of the second fastening portion is spaced apart from the junction;
wherein the first arm strap is configured to support one of the wrist and/or the forearm of the user and the loop of the second arm strap is configured to support the other of the wrist and/or the forearm of the same arm of the user,
wherein the single neck strap is between about 14 inches and about 20 inches in length, the first arm strap and the second arm strap are each between about 21 inches and about 33 inches in length, and the single neck strap, the first arm strap, and the second arm strap are each between about ½ inch wide and about 2 inches wide.

13. A method of adjusting an arm sling for supporting a wrist and/or a forearm of a user, the method comprising:
providing an arm sling for supporting a wrist and/or a forearm of a user, including:
a single neck strap having a first end and a second end;
a gripping sleeve through which the single neck strap is disposed, the gripping sleeve being an elongate tube;
a first arm strap configured to be reversibly coupled to the first end of the single neck strap; and
a second arm strap configured to be reversibly coupled to the second end of the single neck strap, the second arm strap including:
a belt configured to be selectively slidably connected to the second end of the single neck strap, the belt including a first fastening portion;
a loop with an inner surface and an outer surface and joined to the belt at a junction, the loop including a second fastening portion, the first fastening portion configured to removably connect with the second fastening portion at a plurality of locations along a length of the second fastening portion to selectively vary a distance between the loop and the second end of the single neck strap, the loop configured be positioned around and to support the wrist and/or the forearm of the user, wherein the loop is coupled to the belt and the belt is reversibly coupled to the single neck strap; and
a securement band disposed adjacent the junction joining the belt and the loop, the securement band affixed to the loop and configured to selectively hold the belt adjacent to the loop, wherein the securement band is attached to the inner surface of the loop;
wherein the first arm strap is configured to support one of the wrist and/or the forearm of the user and the loop of the second arm strap is configured to support the other of the wrist and/or the forearm of the same arm of the user,
wherein the single neck strap is between about 14 inches and about 20 inches in length, the first arm strap and the second arm strap are each between about 21 inches and about 33 inches in length, and the single neck strap, the first arm strap, and the second arm strap are each between about ½ inch wide and about 2 inches wide;
disposing the second arm strap about one of the wrist and/or the forearm of the user;
removably connecting the first fastening portion with the second fastening portion to selectively vary the distance between the loop and the second end of the single neck strap.

14. The method of claim 13, further comprising a step of closing the securement band around the loop and the belt following the step of removably connecting the first fastening portion with the second fastening portion to selectively vary the distance between the loop and the second end of the single neck strap.

* * * * *